(12) United States Patent
Winchester

(10) Patent No.: US 6,589,224 B2
(45) Date of Patent: Jul. 8, 2003

(54) METHOD OF INTRODUCING FLUIDS INTO A PATIENT'S BODY

(75) Inventor: James Winchester, McLean, VA (US)

(73) Assignee: Renal Tech International LLC, New York, NY (US)

( * ) Notice: Subject to any disclaimer, the term of this patent is extended or adjusted under 35 U.S.C. 154(b) by 3 days.

(21) Appl. No.: 09/782,006

(22) Filed: Feb. 14, 2001

(65) Prior Publication Data

US 2002/0111593 A1 Aug. 15, 2002

(51) Int. Cl.$^7$ .............................................. A61M 31/00
(52) U.S. Cl. ........................ 604/506; 604/507; 604/126; 604/406
(58) Field of Search ............................... 604/4.01, 5.04, 604/6.09, 6.15, 6.16, 500, 506–508, 80, 126, 190, 251, 252, 406, 85, 7; D24/162

(56) References Cited

U.S. PATENT DOCUMENTS

| | | | | | |
|---|---|---|---|---|---|
| 2,835,392 A | * | 5/1958 | Hamilton | ................... | 210/477 |
| 2,904,857 A | * | 9/1959 | Goetz | ........................ | 210/239 |
| 3,882,026 A | * | 5/1975 | McPhee | ..................... | 210/446 |
| 4,066,556 A | * | 1/1978 | Vaillancourt | ................ | 210/448 |
| 5,419,770 A | * | 5/1995 | Crass et al. | ................. | 604/118 |
| 5,439,587 A | * | 8/1995 | Stankowski et al. | ... | 210/321.64 |
| 5,545,131 A | * | 8/1996 | Davankov | ................... | 210/646 |
| 5,936,061 A | * | 8/1999 | Andersson et al. | ......... | 210/679 |
| 6,087,300 A | * | 7/2000 | Davankov et al. | .......... | 502/402 |

* cited by examiner

*Primary Examiner*—David A. Scherbel
*Assistant Examiner*—Patrick Buechner
(74) *Attorney, Agent, or Firm*—I. Zborovsky

(57) ABSTRACT

A method of introducing a fluid into a patient's body has the steps of accommodating the fluid in a plastic container, connecting an introducer to the plastic container so that the fluid can flow from the plastic container through the introducer into a patient's body, and arranging an adsorbing material between the plastic container and the introducer so that the fluid flows from the plastic container first through the adsorbing material, at least some toxins from the fluid are adsorbed by and retained on the adsorbing material, while the fluid purified from at least some toxins is introduced by the introducer into a patient's body.

6 Claims, 2 Drawing Sheets

METHOD OF INTRODUCING FLUIDS INTO A PATIENT'S BODY

BACKGROUND OF THE INVENTION

The present invention relates to a method of introducing fluids into a patient's body.

It is known that various fluids are introduced into a patient's body for prophylaxis and treatment, such as blood, nutrient solution, medications, etc. Usually the fluids are introduced from plastic containers, It has been found that the plastic materials of the containers are subjected to deterioration with resulting discharge of chemical components into the fluid, which components thereafter are entrained in the fluids and introduced in the patient's body and cause significant negative effects. Such components are for example furfurals, etc.

SUMMARY OF THE INVENTION

Accordingly, it is an object of the present invention to provide a method of introduction of fluids into a patient's body which avoids the disadvantages of the prior art.

In keeping with these objects and with others which will become apparent hereinafter, one feature of present invention resides in a method of introducing a fluid into a patient's body, comprising the steps of holding a fluid in a plastic container; connecting the plastic container with an introducing element through which the fluid is introduced from the plastic container into a patient's body; and arranging between the plastic container and the introducer an adsorbing material through which the fluid passes so that at least some toxins contained in the fluid are adsorbed by the adsorbing material and the fluid purified from at least some of toxins is introduced into the patient's body through the introducer.

When the method is performed in accordance with the present invention, then a fluid which is introduced into the body into the patient's body is first purified by the adsorbing material which adsorbs and retains at least some toxins from the fluid, and then the purified fluid is introduced in the patient's body.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF PREFERRED EMBODIMENTS

Figure 1:
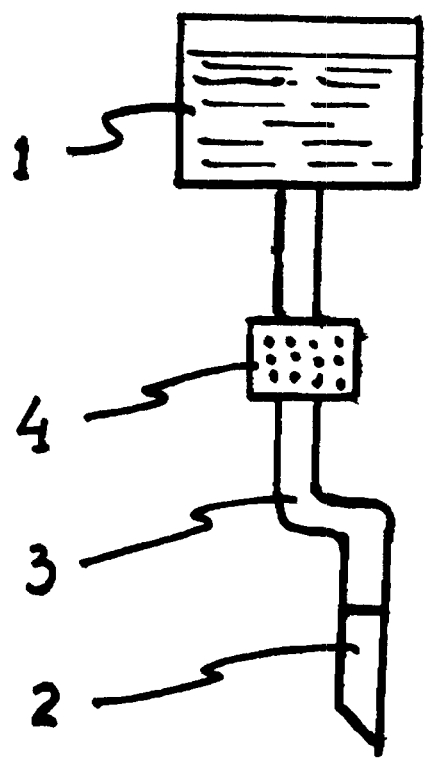
FIG. 1 is a view illustrating a method of introducing fluids into a patient's body in accordance with the first embodiment of the present invention.

As shown in FIG. 1 an introducing device for performing the inventive method has a container in which a fluid to be introduced into a patient's body is accommodated and is identified as a whole with reference numeral 1. The container 1 is composed of a plastic material, as known per se in the art.

The introducing device for performing the inventive method further has an introducer which is identified as a whole with reference numeral 2. The introducer can be formed as any introducing instrument, such as a syringe, a needle, etc. which is also well known in the art. The introducer 2 is connected with the plastic container 1 by a connecting line 3.

In accordance with the present invention, the introducing device for performing the inventive method is provided with an adsorbing material which is identified as a whole with reference numeral 4. The adsorbing material is located between the plastic container 1 and the introducer 2, so that when the fluid flows from the plastic container 1 to the introducer 2, it passes through the adsorbing material 4. The adsorbing material is selected so that it adsorbs toxic components, which can be discharged by the plastic material of the container 1, for example for furfurals, etc. For this purpose the adsorbing material 4 can be for example a material composed of porous hydrophobic divinylbenzene copolymer which initially has surface exposed vinyl groups in which thereafter the vinyl groups are chemically modified so as to form different surface exposed functional groups which are hydrophilic and biocompatible, as disclosed for example in U.S. Pat. Nos. 6,087,300; 6,114,466; 6,133,393; 6,136,424, and 6,157,707. This material can be produced as disclosed in the above listed patents, which are incorporated here by means of a reference.

In the embodiment shown in FIG. 1, the adsorbing material is accommodated in a portion of the line 3. It can be inserted in the portion of the line 3, or can be formed as small container, cartridge, etc. located in a certain region of the line and connected to an upstream part of the line and a downstream part of the line correspondingly, as shown in FIG. 1.

Figure 2:
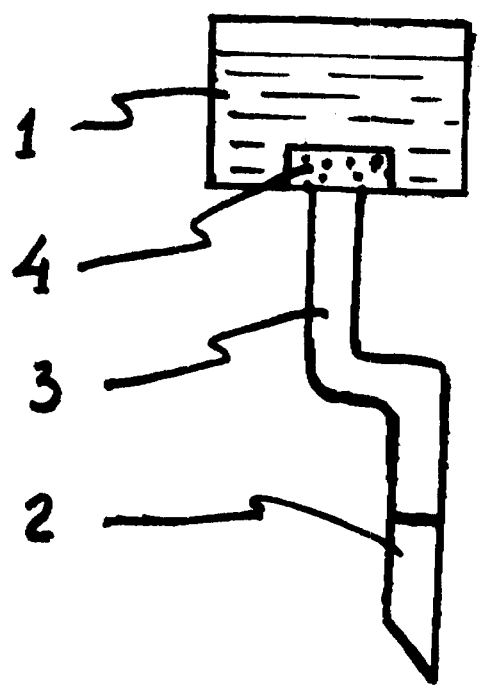
FIG. 2 is a view illustrating a method in accordance with the second embodiment of the present invention.

FIG. 2 shows another embodiment of the. The device for performing the inventive method also has the plastic container 1, the introducer 2, the line connecting the plastic container 1 with the introducer 2, and the adsorbing material 4. Here, however, the adsorbing material 4 is associated with the plastic container 1. For example, it can be arranged on the bottom of the plastic container 1, so that when the plastic container is being emptied, the fluid passes first through the adsorbing material 4 before entering the line 3, and thereby the toxins from the fluid are adsorbed by and retained in the adsorbing material.

Figure 3:
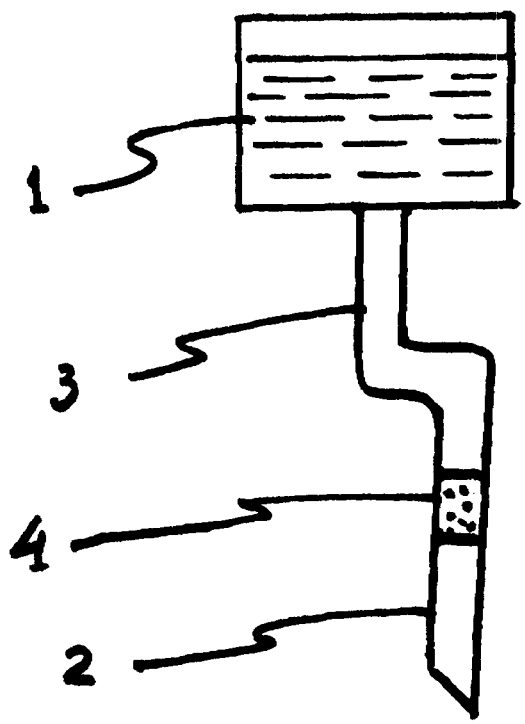
FIG. 3 is a view illustrating a method in accordance with the third embodiment of the present invention.
Figure 4:
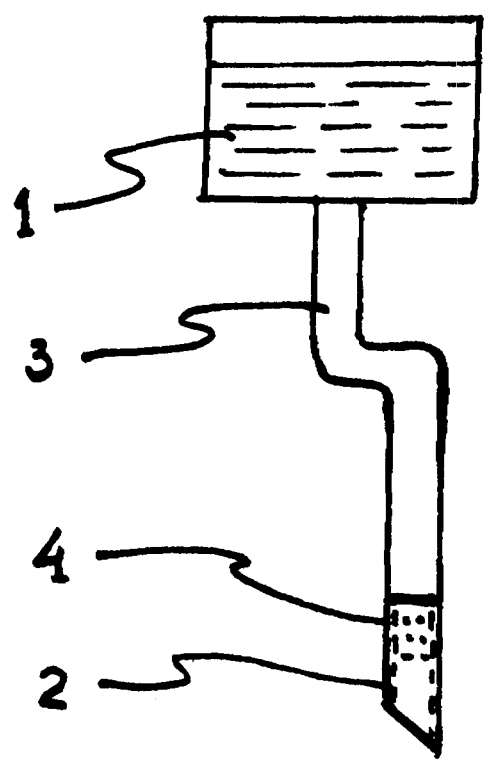
FIG. 4 is a view illustrating a method in accordance with a fourth embodiment of the present invention.

The embodiment shown in FIG. 3 is substantially similar to the embodiment shown in the preceding figures with some distinction. In particular, the device shown in FIG. 3 also has the plastic container 1, the introducer 2, the connecting line 3 and the adsorbing material 4. However, in this embodiment the adsorbing material 4 is associated with the introducer 3. In particular, it is arranged immediately upstream of the introducer and connected to it. In this device, the fluid which flows from the plastic container 1 through the line 3 is detoxified before entering the introducer 2, since toxins from the fluid are adsorbed by and retained on the adsorbing material 4, while the purified fluid flows into the introducer 2 and then into the body of the patient.

It will be understood that each of the elements described above, or two or more together, may also find a useful application in other types of constructions differing from the types described above.

While the invention has been illustrated and described as embodied in method of and device for introducing fluids into a patient's body, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of introducing a fluid into a patient's body, comprising the steps of accommodating the fluid in a plastic container; connecting an introducer for directly introducing the fluid into a patient's body, to said plastic container by a connecting line which extends from the plastic container to the introducer, so that the fluid can flow from the plastic container through the connecting line into the introducer and from the introducer into a patient's body; and, before introduction of the fluid by the introducer into a patient's body, adsorbing at least some toxic components discharged by a plastic material of the plastic container, so that the fluid purified from the at least some toxic components discharged by the plastic material of the container is introduced by the introducer into a patient's body.

2. A method of introducing a fluid into a patient's body as defined in claim 1, wherein said adsorbing includes arranging an adsorbing material which adsorbs at least some toxic components discharged by the plastic material of the container, exclusively on a bottom of the plastic container, from which bottom said connecting line extends.

3. A method of introducing a fluid into a patient's body as defined in claim 1, wherein said adsorbing includes arranging an adsorbing material which adsorbs at least some toxic components discharged by the plastic material of the plastic container, directly inside the introducer.

4. A method of introducing a fluid into a patient's body as defined in claim 1, wherein said adsorbing includes arranging an adsorbing material which adsorbs at least some toxic components discharged by the plastic material of the plastic container, in the connecting line.

5. A method of introducing a fluid into a patient's body as defined in claim 1, wherein said adsorbing includes arranging an adsorbing material which adsorbs at least some toxic components discharged by the plastic material of the plastic container, upstream of said introducer.

6. A method of introducing a fluid into a patient's body as defined in claim 1, wherein adsorbing includes adsorbing furfurals which are discharged from the plastic material of the plastic container.

\* \* \* \* \*